United States Patent
Park et al.

(10) Patent No.: US 10,088,408 B2
(45) Date of Patent: Oct. 2, 2018

(54) FRICTION COEFFICIENT MEASURING METHOD OF SURFACE OF SPECIMEN

(71) Applicants: Hyundai Motor Company, Seoul (KR); Pusan National University Industry—University Cooperation Foundation, Busan (KR)

(72) Inventors: Jung Yeon Park, Gyeonggi-Do (KR); Woong Pyo Hong, Seoul (KR); Ji Youn Seo, Gyeonggi-do (KR); Bo Kyung Kim, Gyeonggi-do (KR); In Woong Lyo, Gyeonggi-do (KR); Kwang Hoon Choi, Gyeonggi-do (KR); Doo In Kim, Busan (KR); Sung Mo Park, Busan (KR); Myung Yung Jeong, Busan (KR)

(73) Assignees: Hyundai Motor Company, Seoul (KR); Pusan National University Industry—University Cooperation, Busan (KR)

( * ) Notice: Subject to any disclaimer, the term of this patent is extended or adjusted under 35 U.S.C. 154(b) by 366 days.

(21) Appl. No.: 14/944,276

(22) Filed: Nov. 18, 2015

(65) Prior Publication Data

US 2016/0161396 A1 Jun. 9, 2016

(30) Foreign Application Priority Data

Dec. 5, 2014 (KR) .......................... 10-2014-0174073

(51) Int. Cl.
*G01N 19/02* (2006.01)
*G01Q 60/24* (2010.01)
(Continued)

(52) U.S. Cl.
CPC ............. *G01N 19/02* (2013.01); *G01Q 30/06* (2013.01); *G01Q 60/26* (2013.01)

(58) Field of Classification Search
CPC ...................................................... G01N 19/02
(Continued)

(56) References Cited

U.S. PATENT DOCUMENTS 5,400,647 A * 3/1995 Elings .................... G01Q 10/06
73/105
8,342,008 B2 1/2013 Baba et al.
(Continued)

FOREIGN PATENT DOCUMENTS

| JP | H08146019 A | 6/1996 |
| JP | 2005535903 A | 11/2005 |

(Continued)

OTHER PUBLICATIONS

Palacio, Manuel L.B., et al., "Normal and Lateral Force Calibration Techniques for AFM Cantilevers", Critical Reviews in Solid State and Materials Sciences, 35:73-104, 2010.
(Continued)

*Primary Examiner* — Walter L Lindsay, Jr.
*Assistant Examiner* — Philip Marcus T Fadul
(74) *Attorney, Agent, or Firm* — Mintz Levin Cohn Ferris Glovsky and Popeo, P.C.; Peter F. Corless

(57) ABSTRACT

A method of measuring a friction coefficient of a surface of a specimen includes: obtaining surface information of the specimen by using an atomic force microscope (AFM); calculating data of a friction coefficient of the surface of the specimen by using the surface information of the specimen; and mapping the data of the friction coefficient of the specimen to an image. The method of measuring a friction coefficient of a surface of a specimen may prevent a probe part of an atomic force microscope from being worn out and secure high reliability of the friction coefficient value by (Continued)

correcting the atomic force microscope using a specimen to be actually measured and measuring a fiction coefficient at the same time.

7 Claims, 4 Drawing Sheets

(51) Int. Cl.
   *G01Q 30/06* (2010.01)
   *G01Q 60/26* (2010.01)
(58) Field of Classification Search
   USPC .............................................................. 73/9
   See application file for complete search history.

(56) References Cited

U.S. PATENT DOCUMENTS

| 8,844,061 | B2 | 9/2014 | Baba et al. | |
|---|---|---|---|---|
| 2007/0218383 | A1* | 9/2007 | Seshita | G03G 9/0806 |
| | | | | 430/108.1 |
| 2007/0266780 | A1 | 11/2007 | Baba et al. | |
| 2013/0047302 | A1 | 2/2013 | Noel et al. | |
| 2014/0298548 | A1 | 10/2014 | Baba et al. | |

FOREIGN PATENT DOCUMENTS

| JP | 2007-309919 A | 11/2007 |
|---|---|---|
| JP | 2009-150696 A | 7/2009 |
| JP | 2013-525806 A | 6/2013 |
| KR | 10-2001-0069616 A | 7/2001 |
| KR | 10-2006-0050222 A | 5/2006 |
| KR | 10-2006-0078681 A | 7/2006 |
| KR | 10-2012-0126193 A | 11/2012 |

OTHER PUBLICATIONS

Varenberg, M., et al., "An improved wedge calibration method for lateral force in atomic force microscopy", Review of Scientific Instruments, vol. 74, No. 7, pp. 3362-3367, Jul. 2003.

Munz, M., "Force Calibration in Lateral Force Microscopy—A Review of the Experimental Methods", Journal of Physics D Applied Physics, 43 (2010) 063001, pp. 1-88.

* cited by examiner

FRICTION COEFFICIENT MEASURING METHOD OF SURFACE OF SPECIMEN

CROSS-REFERENCE TO RELATED APPLICATION

This application is based on and claims the benefit of priority to Korean Patent Application No. 10-2014-0174073, filed on Dec. 5, 2014 in the Korean Intellectual Property Office, the invention of which is incorporated herein in its entirety by reference.

TECHNICAL FIELD

The present invention relates to a method of measuring a friction coefficient of a surface of a specimen.

BACKGROUND

Generally, an atomic force microscope (AFM) has been used to measure a shape of a surface of a specimen.

The AFM images the surface of the specimen by measuring deformation of a cantilever, a voltage value from a probe, and the like, which are generated by pressing the surface of the specimen with the probe installed at an end of a structure of a cantilever shape.

However, since a height and a shape are different from the AFM depending on the specimen, there is a need to correct force applied in a direction parallel to the surface of the specimen or in a lateral direction.

According to the related art, after the AFM is corrected using a separate reference specimen, a shape of a surface of an actual object to be measured has been measured. However, there was a problem that the probe is easily worn out or damaged due to a frequent use.

SUMMARY

In preferred aspects, the present invention provides a method of measuring a friction coefficient of a surface of a specimen. In particular, the method may prevent a probe part of an atomic force microscope (AFM) from being worn out and secure high reliability of the measuring the friction coefficient value, by correcting the atomic force microscope using a specimen to be actually measured and measuring a fiction coefficient at the same time.

According to an exemplary embodiment of the present invention, the method of measuring a friction coefficient of a surface of a specimen may include: 1) obtaining a surface information of a specimen by using an atomic force microscope (AFM); 2) calculating data of a friction coefficient of the surface of the specimen by using the surface information of the specimen; and 3) mapping the data of the friction coefficient of the specimen into an image.

In obtaining the surface information, a voltage value may be obtained by force applied to the surface of the specimen from the atomic force microscope (AFM).

The method of measuring a friction coefficient may further include correcting the surface information of the specimen obtained by using the atomic force microscope.

In the correcting the surface information of the specimen, the method may include: measuring a slope angle and viscosity of a slope surface of the specimen, and viscosity of a flat plane of the specimen; and correcting the surface information of the specimen by using information of the measured slope angle and viscosity of the slope surface, and viscosity of the flat plane.

In correcting the surface information, the corrected information may be obtained by multiplying the surface information of the specimen with a correction constant α, and the correction constant may be determined by the following Equation 2.

$$\alpha = \frac{\mu_S(L + A_S\cos\theta)}{W_S(\cos^2\theta - \mu_S^2\sin^2\theta)} \quad \text{[Equation 2]}$$

In Equations 2, α is a correction constant, $\mu_S$ is a friction coefficient of a slope surface, L is force applied to the specimen from the atomic force microscope, θ is a slope angle of the slope surface, $A_S$ is viscosity of the slope surface, and $W_S$ is a half of a voltage value measured by the atomic force microscope from the slope surface.

Further, in correcting the surface information, the friction coefficient $\mu_S$ of the slope surface may be determined by the following Equation 1.

$$\mu_S^2\sin\theta(L\cos\theta + A_S) - \frac{\Delta_S}{W_S}(L + A_S\cos\theta)\mu_S + L_S\sin\theta\cos\theta = 0 \quad \text{[Equation 1]}$$

In Equations 1, $\mu_S$ is the friction coefficient of the slope surface, L is force applied to the specimen from the atomic force microscope, θ is the slope angle of the slope surface, $A_S$ is viscosity of the slope surface, WS is a half of a voltage value measured by the atomic force microscope from the slope surface, and $\Delta_S$ is a voltage value measured by the atomic force microscope from the slope surface.

In correcting the surface information, friction coefficients of two slope surfaces may be obtained by the Equation 1 and two correction constants may be obtained by the Equation 2, and a friction coefficient of a plane of the specimen may be obtained by the following Equation 3 and any one of the two correction constants may be selected by using the obtained friction coefficient.

$$\mu_{flat} = \frac{\alpha W_{flat}}{(L + A_{flat})} \quad \text{[Equation 3]}$$

In Equations 3, $\mu_{flat}$ is the friction coefficient of the plane, α is the correction constant, L is force applied to the specimen from the atomic force microscope, $A_{flat}$ is viscosity of the plane, and $W_{flat}$ is a half of the voltage value measured by the atomic force microscope from the plane.

Each of two values of the friction coefficients of the plane of the specimen obtained by the Equation 3 and each of two values of friction coefficients of the slope surface obtained by the Equation 1 may be compared and a value of the correction constant corresponding to a case in which a difference is a minimum may be selected to correct the surface information of the specimen.

In calculating the data of a friction coefficient of the surface of the specimen, the data of the friction coefficient may be determined by the following Equation 5.

$$\mu = \frac{\alpha W}{(L + A)} \quad \text{[Equation 5]}$$

In Equations 5, μ is the friction coefficient of the specimen, α is the correction constant, L is force applied to the specimen from the atomic force microscope, A is viscosity of the surface of the specimen, and W is a half of the voltage value measured by the atomic force microscope.

BRIEF DESCRIPTION OF THE DRAWINGS

The above and other objects, features and advantages of the present invention will be more apparent from the following detailed description taken in conjunction with the accompanying drawings.

DETAILED DESCRIPTION

Hereinafter, a friction coefficient measuring method of a surface of a specimen according to an exemplary embodiment of the present invention will be described in detail with reference to the accompanying drawings.

Figure 1:
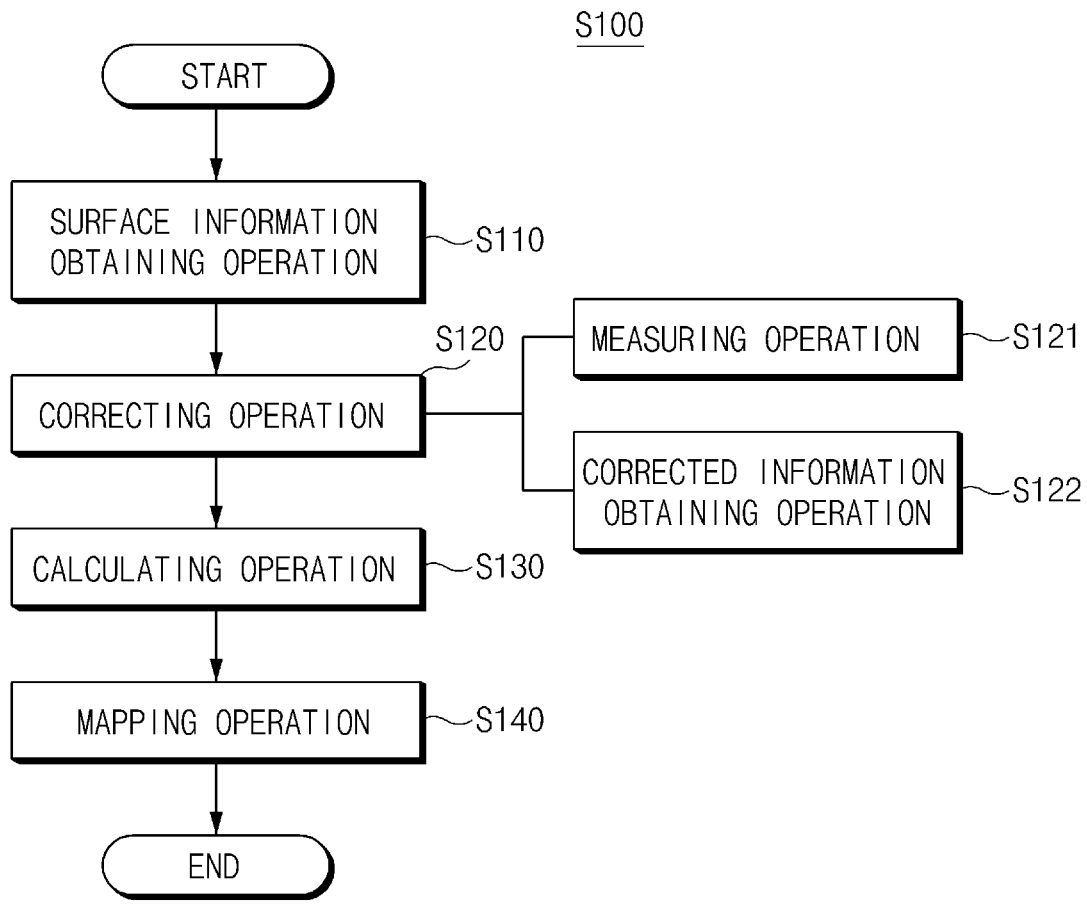
FIG. 1 is an exemplary schematic flow chart of method of measuring a friction coefficient of a surface of a specimen according to an exemplary embodiment of the present invention.

FIG. 1 is an exemplary schematic flow chart of a friction coefficient measuring method of a surface of a specimen according to an exemplary embodiment of the present invention.

Referring to FIG. 1, a method of measuring a friction coefficient S100 of a surface of a specimen according to an exemplary embodiment of the present invention may measure the friction coefficient and friction force of any surface of the specimen using an atomic force microscope (AFM). The method may include: a surface information obtaining operation S110 to obtain a surface information of a specimen by using an atomic force microscope (AFM); a correcting operation S120 to calculate data of a friction coefficient of the surface of the specimen by using the surface information of the specimen; a calculating operation S130, and a mapping operation S140 to map the data of the friction coefficient of the specimen into an image.

In the surface information obtaining operation S110, the surface information of a specimen 10 to be measured may be obtained. In particular, a surface of the specimen 10 may be measured by using an atomic force microscope (AFM).

The atomic force microscope used in an exemplary embodiment of the present invention may obtain the surface information of the specimen 10 by a manner in which when a probe is attached to an end of a structure of a cantilever shape and is in contact with the surface of the specimen 10 to be measured, the forces of attraction and repulsion may act between atoms of the surface of the specimen 10 depending on an interval between the atoms and a degree of bending of the cantilever by the above-mentioned forces may be measured. In this case, the voltage information measured from the probe may be simultaneously measured.

In the surface information obtaining operation S110, lateral force may be pressurized to the surface of the specimen 10 and an amount of voltage measured by the probe may be measured from the surface of the specimen at the same time by using the atomic force microscope. Hereinafter, the surface information of the specimen 10 according to an exemplary embodiment of the present invention means a voltage value measured from each surface of the specimen by the atomic force microscope.

In the correcting operation S120, the surface information of the specimen 10 obtained by using the atomic force microscope in the surface information obtaining operation S110 may be corrected. The correcting operation S120 may include a measuring operation S121 to measure a slope angle and viscosity of a slope surface of the specimen, and viscosity of a flat plane of the specimen and a corrected information obtaining operation S122 to correct the surface information of the specimen by using information of the measured slope angle and viscosity of the slope surface, and viscosity of the flat plane.

The atomic force microscope may obtain the surface information by the manner in which the probe applies the lateral force to the surface of the specimen 10. Since the applied lateral force differently may act depending on a shape and height of the surface of the specimen 10, the surface information of the specimen may need to be corrected taking account of the height and shape of the surface of the specimen 10 in order to calculate data of a friction coefficient having high reliability.

Accordingly, for purpose of the above mentioned object, in the measuring operation S121, data required to correct the surface information of the specimen may be measured, and in the corrected information obtaining operation S122, the corrected data may be secured by multiplying the voltage information measured from the surface of the specimen with a predetermined correction constant α and the correction constant α required to secure the corrected data may be calculated. Hereinafter, the measuring operation S121 will be described and the corrected information obtaining operation S122 will be then described.

Figure 2:
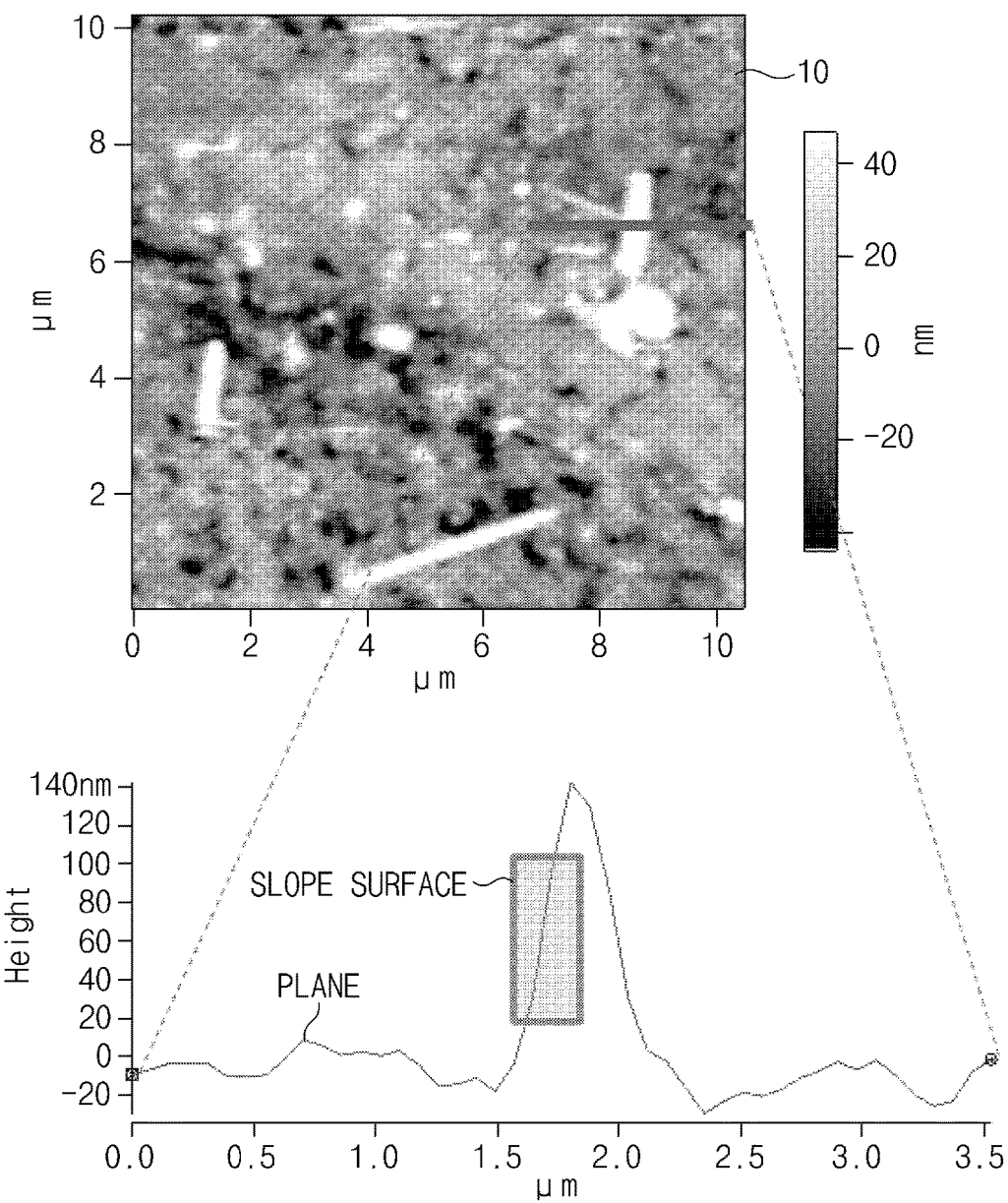
FIG. 2 is exemplary image and graph of information obtained by measuring \the friction coefficient of the surface of the specimen of FIG. 1 according to an exemplary embodiment of the present invention.

FIG. 2 shows exemplary information and graph obtained in the measuring operation S121 for the specimen of FIG. 1.

Referring to FIG. 2, in the measuring operation S121, data required to obtain the correction constant α may be measured. In the present operation S121, a slope angle $\theta_S$ of a slope surface forming a slope of the surface of the specimen 10, and viscosity $A_S$ of the corresponding slope surface and viscosity $A_{flat}$ of a flat plane may be measured.

Since the S121 operation may secure the data for securing a value of the correction constant α, the slope surface of the specimen to be measured may not be limited as long as it is a region having a slope of a predetermined angle.

In the corrected information obtaining operation S122, the correction constant α may be obtained by using information of slope angle and viscosity measured in the measuring operation S121 described above.

First, in the S122 operation, a friction coefficient $\mu_S$ at the slope surface from which the slope angle and viscosity are measured may be calculated by using the following Equation 1.

$$\mu_S^2 \sin\theta(L\cos\theta + A_S) - \frac{A_S}{W_S}(L + A_S\cos\theta)\mu_S + L_S\sin\theta\cos\theta = 0 \quad \text{[Equation 1]}$$

In Equation 1, $\mu_S$ is a friction coefficient of a slope surface, L is force applied to the specimen from the atomic force microscope, θ is an slope angle of the slope surface, $A_S$ is viscosity of the slope surface, $W_S$ is a half of a voltage value measured by the atomic force microscope from the slope surface, and $\Delta_S$ is a voltage value measured by the atomic force microscope from the slope surface.

Since Equation 1 is a quadratic equation for the friction coefficient $\mu_S$, if Equation 1 is solved, values of two different friction coefficients $\mu_{S1}$ and $\mu_{S2}$ may be obtained.

A value of the correction constant α may be calculated by using the following Equation 2.

$$\alpha = \frac{\mu_S(L + A_S\cos\theta)}{W_s(\cos^2\theta - \mu_S^2\sin^2\theta)} \quad \text{[Equation 2]}$$

In Equation 2, α is the correction constant, $\mu_S$ is the friction coefficient of the slope surface, L is force applied to the specimen from the atomic force microscope, θ is the slope angle of the slope surface, $A_S$ is viscosity of the slope surface, and $W_S$ is a half of the voltage value measured by the atomic force microscope from the slope surface.

However, since the two friction coefficients $\mu_{S1}$ and $\mu_{S2}$ are calculated in Equation 1, if the two friction coefficients are substituted into Equation 2, two correction constants $\alpha_1$ and $\alpha_2$ corresponding to the respective friction coefficients $\mu_{S1}$ and $\mu_{S2}$ may be calculated.

For obtaining any one of the two correction constants, a friction coefficient of a flat plane may be calculated by using the following Equation 3.

$$\mu_{flat} = \frac{\alpha W_{flat}}{(L + A_{flat})} \quad \text{[Equation 3]}$$

In Equation 3, $\mu_{flat}$ is a friction coefficient of a plane, α is the correction constant, L is force applied to the specimen from the atomic force microscope, $A_{flat}$ is viscosity of the plane, and $W_{flat}$ is a half of the voltage value measured by the atomic force microscope from the plane.

If the two correction constants $\alpha_1$ and $\alpha_2$ are substituted into Equation 3, friction coefficients $\mu_{flat1}$ and $\mu_{flat}$ at two flat planes may be calculated.

In particular, a difference between values between the friction coefficients corresponding to each other may be calculated and the correction constant corresponding to a case in which the difference is minimum may be selected, which may be used for the correction.

That is, by comparing a value of $|\mu_{flat1} - \mu_{S1}|$ and a value of $|\mu_{flat2} - \mu_{S2}|$, the correction constant corresponding to a case having a relatively small value may be selected. For example, when it is assumed that $|\mu_{flat1} - \mu_{S1}|$ has a smaller value, $\alpha_1$ is selected as the correction constant to correct the surface information of the specimen.

The surface information of the specimen 10 v corrected by using the following Equation 4.

$$W_C = \alpha W \quad \text{[Equation 4]}$$

In Equation 4, $W_C$ is surface information of a corrected specimen, α is a finally determined correction constant, and W is surface information of an actually measured specimen.

In the S122 operation, the surface information of the specimen 10 which is corrected to have improved reliability may be obtained.

In the calculating operation S130, a friction coefficient μ of the surface of the specimen 10 may be obtained by using the corrected surface information of the specimen.

In the S130 operation, the friction coefficient μ of the surface of the specimen 10 may be calculated by using the following Equation 5.

$$\mu = \frac{\alpha W}{(L + A)} \quad \text{[Equation 5]}$$

In Equation 5, μ is the friction coefficient of the specimen, α is the correction constant, L is force applied to the specimen from the atomic force microscope, A is viscosity of the surface of the specimen, and W is a half of the voltage value measured by the atomic force microscope.

Meanwhile, viscosity at the entire surface of the specimen required from Equation 5 may also be obtained in the surface information obtaining operation S111 and may also be obtained in the measuring operation S121 described above, or may also be separately obtained in the present calculating operation S130.

Figure 3:
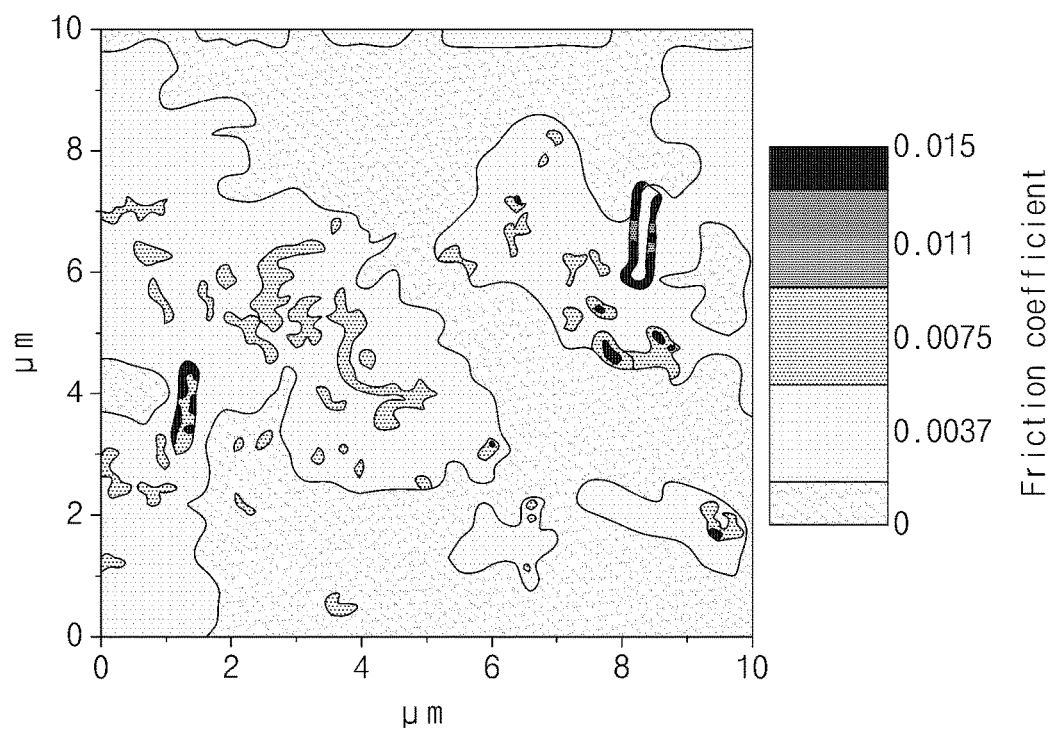
FIG. 3 is an exemplary friction coefficient map obtained by mapping the data of the friction coefficient of the surface of the specimen of FIG. 1 according to an exemplary embodiment of the present invention.
Figure 4:
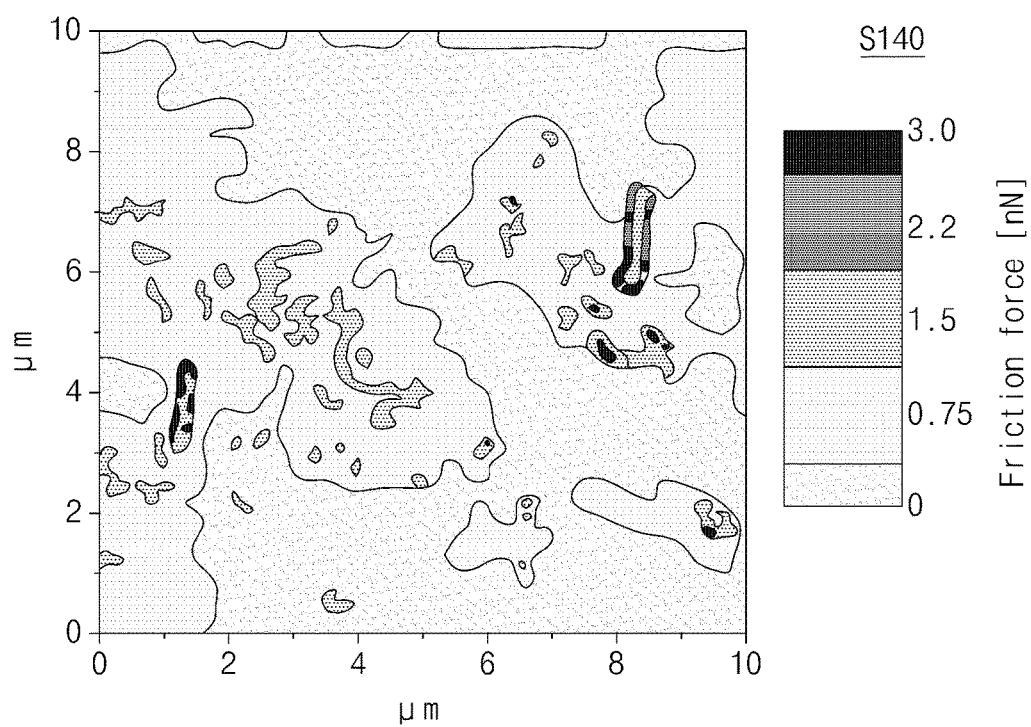
FIG. 4 is an exemplary friction force map mapped by using the friction coefficient map obtained by mapping the data of the friction coefficient of the surface of the specimen of FIG. 1 according to an exemplary embodiment of the present invention.

FIG. 3 show an exemplary friction coefficient map obtained in an exemplary mapping operation S140 for the surface of the specimen of FIG. 1, and FIG. 4 is an exemplary friction force map mapped by using the friction coefficient map obtained in the mapping operation for the surface of the specimen of FIG. 1.

In the mapping operation S140, a map mapped in an image may be obtained by using a finally calculated friction coefficient μ. That is, as shown in FIG. 3, according to the S140 operation, the map in which the value of the friction coefficient of the surface of the specimen is mapped may be manufactured.

In addition, as shown in FIG. 4, a map in which a friction force value itself is mapped by using the map of the calculated friction coefficient as well as the map of the friction coefficient may also be manufactured.

As described above, according to the exemplary embodiment of the present invention, the method of measuring the friction coefficient of the surface of the specimen may reduce wear of the probe and may be provided by correcting the atomic force microscope using the surface of the specimen to be measured while excluding a separate correction specimen.

In addition, the map in which the friction coefficient and friction force of the surface of the specimen are imaged may be easily manufactured.

However, the present invention is not limited to the exemplary embodiments described above, but may be implemented in various exemplary embodiments within the accompanying claims. The present invention is within the scope of the following claims up to various modified ranges by those skilled in the art to which the present invention pertains without departing from the gist of the present invention.

What is claimed is:

1. A method of measuring a friction coefficient of a surface of a specimen, comprising:
    obtaining surface information of the specimen by using an atomic force microscope (AFM);
    calculating data of a friction coefficient of the surface of the specimen by using the surface information of the specimen;
    mapping the data of the friction coefficient of the specimen into an image; and correcting the surface information of the specimen obtained by using the atomic force microscope (AFM),
wherein in correcting the surface information, the method includes:
measuring a slope angle and viscosity of a slope surface of the specimen, and viscosity of a flat plane of the specimen; and
correcting the surface information of the specimen by using information of the measured slope angle and viscosity of the slope surface, and viscosity of the flat plane.

2. The method according to claim 1, wherein in obtaining the surface information of the specimen, a voltage value by a force applied to the surface of the specimen from the atomic force microscope (AFM) is obtained.

3. The method according to claim 1, wherein in correcting the surface information, the corrected information is obtained by multiplying the surface information of the specimen with a correction constant $\alpha$, and
the correction constant is determined by the following Equation 2, $$\alpha = \frac{\mu_S(L + A_S\cos\theta)}{W_S(\cos^2\theta - \mu_S^2\sin^2\theta)} \quad \text{[Equation 2]}$$

wherein $\alpha$ is a correction constant, $\mu_S$ is a friction coefficient of a slope surface, L is force applied to the specimen from the atomic force microscope, $\theta$ is a slope angle of the slope surface, $A_S$ is viscosity of the slope surface, and $W_S$ is a half of a voltage value measured by the atomic force microscope from the slope surface.

4. The method according to claim 3, wherein in correcting the surface information, the friction coefficient $\mu_S$ of the slope surface is determined by the following Equation 1, $$\mu_S^2\sin\theta(L\cos\theta + A_S) - \frac{\Delta_S}{W_S}(L + A_S\cos\theta)\mu_S + L_S\sin\theta\cos\theta = 0 \quad \text{[Equation 1]}$$

wherein $\mu_S$ is the friction coefficient of the slope surface, L is force applied to the specimen from the atomic force microscope, $\theta$ is the slope angle of the slope surface, $A_S$ is viscosity of the slope surface, $W_S$ is a half of a voltage value measured by the atomic force microscope from the slope surface, and $\Delta_S$ is a voltage value measured by the atomic force microscope from the slope surface.

5. The method according to claim 4, wherein in correcting the surface information,
friction coefficients of two slope surfaces are obtained by the Equation 1 and two correction constants are obtained by the Equation 2, and
a friction coefficient of a plane of the specimen is obtained by the following Equation 3 and any one of the two correction constants is selected by using the obtained friction coefficient, $$\mu_{flat} = \frac{\alpha W_{flat}}{(L + A_{flat})} \quad \text{[Equation 3]}$$

wherein $\mu_{flat}$ is the friction coefficient of the plane, $\alpha$ is the correction constant, L is force applied to the specimen from the atomic force microscope, $A_{flat}$ is viscosity of the plane, and $W_{flat}$ is a half of the voltage value measured by the atomic force microscope from the plane.

6. The method according to claim 5, wherein each of two values of the friction coefficients of the plane of the specimen obtained by the Equation 3 and each of two values of friction coefficients of the slope surface obtained by the Equation 1 are compared and a value of the correction constant corresponding to a case in which a difference is a minimum is selected to correct the surface information of the specimen.

7. The method according to claim 1, wherein in calculating the data of the friction coefficient of the surface of the specimen, the data of the friction coefficient is determined by the following Equation 5, $$\mu = \frac{\alpha W}{(L + A)} \quad \text{[Equation 5]}$$

wherein $\mu$ is the friction coefficient of the specimen, $\alpha$ is the correction constant, L is force applied to the specimen from the atomic force microscope, A is viscosity of the surface of the specimen, and W is a half of the voltage value measured by the atomic force microscope.

* * * * *